(12) United States Patent
Lee et al.

(10) Patent No.: US 10,204,705 B2
(45) Date of Patent: *Feb. 12, 2019

(54) SYSTEMS AND METHODS FOR DATA CLEANSING SUCH AS FOR OPTIMIZING CLINICAL SCHEDULING

(71) Applicant: Kairoi Healthcare Strategies, Inc., San Francisco, CA (US)

(72) Inventors: Russell D. Lee, Kensington, CA (US); Jeffrey Wu, Madison, WI (US)

(73) Assignee: Kairoi Healthcare Strategies, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/481,744

(22) Filed: Apr. 7, 2017

(65) Prior Publication Data

US 2017/0212994 A1 Jul. 27, 2017

Related U.S. Application Data

(63) Continuation of application No. 15/151,298, filed on May 10, 2016.

(Continued)

(51) Int. Cl.
*G06F 17/30* (2006.01)
*G16H 40/20* (2018.01)
(Continued)

(52) U.S. Cl.
CPC ....... *G16H 40/20* (2018.01); *G06F 17/30117* (2013.01); *G06F 17/30303* (2013.01);
(Continued)

(58) Field of Classification Search
None
See application file for complete search history.

(56) References Cited

U.S. PATENT DOCUMENTS 5,784,635 A * 7/1998 McCallum .......... G06F 17/2705
710/63
7,793,217 B1 * 9/2010 Kim .................... G06F 19/3425
715/255

(Continued)

OTHER PUBLICATIONS

International Search Report and Written Opinion for Related PCT Application PCT/US2016/065963, dated Jan. 30, 2017, pp. 1 to 12.

*Primary Examiner* — Usmaan Saeed
*Assistant Examiner* — Yu Zhao
(74) *Attorney, Agent, or Firm* — Pillsbury Winthrop Shaw Pittman LLP

(57) ABSTRACT

A scheduling system and method for data cleansing may be used to optimize clinical scheduling. The present disclosure describes receiving clinical record data, in an agnostic manner, from a system including a source scheduling database containing the clinical record data; mapping the clinical record data to a desired format; conforming the clinical record data to standardized scheduling elements of the scheduling system; cleansing, in a manner configurable by a user, the clinical record data to purge portions of the clinical record data; providing the clinical record data to an optimization engine for optimization of the clinical record data; optimizing the clinical record data by applying configurable logic to the clinical record data; and uploading one or more newly defined optimized scheduling templates via an outbound connection back to the scheduling system.

12 Claims, 3 Drawing Sheets

Related U.S. Application Data

(60) Provisional application No. 62/269,002, filed on Dec. 17, 2015.

(51) Int. Cl.
- *G16H 10/60* (2018.01)
- *G06Q 10/06* (2012.01)
- *G06Q 50/24* (2012.01)
- *G06F 19/00* (2018.01)
- *G06F 7/00* (2006.01)

(52) U.S. Cl.
CPC .. *G06F 17/30371* (2013.01); *G06F 17/30424* (2013.01); *G06F 17/30563* (2013.01); *G06F 17/30569* (2013.01); *G06F 19/00* (2013.01); *G06Q 10/06311* (2013.01); *G06Q 50/24* (2013.01); *G16H 10/60* (2018.01)

(56) References Cited

U.S. PATENT DOCUMENTS

| | | |
|---|---|---|
| 2002/0099563 A1* | 7/2002 | Adendorff ......... G06F 17/30563 705/7.11 |
| 2006/0247968 A1 | 2/2006 | Kadry |
| 2007/0178501 A1 | 8/2007 | Rabinowitz et al. |
| 2008/0294996 A1* | 11/2008 | Hunt ..................... G06Q 30/02 715/739 |
| 2008/0306926 A1 | 12/2008 | Friedlander et al. |
| 2009/0144088 A1 | 6/2009 | Zubiller et al. |
| 2011/0112867 A1 | 5/2011 | Menschik et al. |
| 2011/0153357 A1 | 6/2011 | Zubiller et al. |
| 2011/0153380 A1* | 6/2011 | Velusamy ............ G06Q 10/109 705/7.19 |
| 2011/0288877 A1 | 11/2011 | Ofek et al. |
| 2012/0029933 A1 | 2/2012 | Zubiller et al. |
| 2012/0059283 A1* | 3/2012 | Gravem ............... A61B 5/0002 600/595 |
| 2012/0059663 A1 | 3/2012 | Levesque et al. |
| 2012/0215560 A1 | 8/2012 | Ofek et al. |
| 2012/0246741 A1 | 9/2012 | Klotz et al. |
| 2013/0291060 A1 | 10/2013 | Moore |
| 2014/0039906 A1 | 2/2014 | Wang et al. |
| 2014/0156302 A1 | 6/2014 | Larsen |
| 2014/0278683 A1* | 9/2014 | Kennell ............ G06Q 10/1053 705/7.19 |
| 2014/0297327 A1 | 10/2014 | Heil et al. |
| 2015/0012300 A1 | 1/2015 | Smith |
| 2015/0012631 A1 | 1/2015 | Udani et al. |
| 2015/0134388 A1 | 5/2015 | Yoo et al. |
| 2015/0332011 A1 | 11/2015 | Ting et al. |
| 2015/0347599 A1 | 12/2015 | Mcmains et al. |
| 2016/0063192 A1 | 3/2016 | Johnson et al. |
| 2016/0217259 A1 | 7/2016 | Chan et al. |
| 2016/0253462 A1* | 9/2016 | Zhong .................. G06F 19/327 |
| 2016/0292369 A1 | 10/2016 | Lakare et al. |
| 2016/0335686 A1 | 11/2016 | Athulurutlrumala et al. |
| 2017/0097647 A1* | 4/2017 | Lunani ..................... C02F 1/00 |

* cited by examiner

SYSTEMS AND METHODS FOR DATA CLEANSING SUCH AS FOR OPTIMIZING CLINICAL SCHEDULING

CROSS-REFERENCE TO RELATED APPLICATIONS

This application is a continuation of and claims priority to U.S. patent application Ser. No. 15/151,298 filed on May 10, 2016, which claims priority to U.S. Provisional Patent Application 62/269,002 filed Dec. 17, 2015, each of which is incorporated by reference in its entirety.

FIELD OF THE DISCLOSURE

This disclosure relates to scheduling systems and methods for data cleansing to optimize clinical scheduling.

BACKGROUND

Scheduling systems are known. Scheduling systems allow professionals to manage scheduling appointments and bookings, among other things. Technical problems are inherent within these current computer systems (e.g., scheduling systems or other systems). For example, when receiving input (e.g., clinical record data or other types of data) from scheduling databases, existing scheduling systems include scheduling products that rely on custom interfaces and application programming interfaces (APIs) for each electronic record the scheduling systems receive as input. An API is code that allows, for example, two software programs to communicate with each other. An API may be used for one or more web-based systems, operating systems, and/or database systems. One example of such input would be electronic medical records (EMRs). Without custom interfaces and APIs, current scheduling systems would only be able to operate on input from certain (or no) scheduling databases. Many scheduling systems are deficient or absent in their capabilities to optimize the scheduling of critical resources. This causes wasted opportunities and may contribute to delayed subject care.

SUMMARY

One aspect of the disclosure may relate to a scheduling system configured for data cleansing to optimize clinical scheduling. The scheduling system may include one or more hardware processors and/or other components. The one or more hardware processors may be configured by machine-readable instructions to receive clinical record data, in an agnostic manner (discussed herein), from a system including a source scheduling database containing the clinical record data. The clinical record data may be mapped to a desired format that may include a plurality of fields. The scheduling system may conform the clinical record data to standardized scheduling elements of the scheduling system. This may be accomplished by parsing the clinical record data. The parsing may include reformatting the clinical record data by assigning portions of the data to appropriate fields.

In addition, one or more hardware processors may be configured to cleanse, in a manner configurable by a user, the clinical record data to purge portions of the clinical record data related to one or more of data errors, data artifacts, business logic, and/or other items. The clinical record data may be provided to an optimization engine for optimization of the clinical record data. Further, the clinical record data may be optimized by applying configurable logic to the clinical record data. Doing so may provide one or more newly defined optimized scheduling templates that configure defined resources such as one or more of providers, rooms, equipment such as X-ray machines and/or EKG monitors for optimal usage of time, where resource availability is matched with customized variables. The customized variables may include one or more of visit complexity, average visit length, number of exam rooms, provider preference, non-physician resources, and/or other information. One or more newly defined optimized scheduling templates may be uploaded via an outbound connection back to the scheduling system.

Another aspect of the disclosure may relate to a method for data cleansing to optimize clinical scheduling. The scheduling method may be performed by one or more hardware processors and/or other components. The one or more hardware processors may be configured by machine-readable instructions to receive clinical record data, in an agnostic manner, from a system including a source scheduling database containing the clinical record data. The clinical record data may be mapped to a desired format that may include a plurality of fields. The scheduling system may conform the clinical record data to standardized scheduling elements of the scheduling system. This may be accomplished by parsing the clinical record data. The parsing may include reformatting the clinical record data by assigning portions of the data to appropriate fields.

In addition, one or more hardware processors may be configured to cleanse, in a manner configurable by a user, the clinical record data to purge portions of the clinical record data related to one or more of data errors, data artifacts, business logic, and/or other items. The clinical record data may be provided to an optimization engine for optimization of the clinical record data. Further, the clinical record data may be optimized by applying configurable logic to the clinical record data. Doing so may provide one or more newly defined optimized scheduling templates that configure one or both of providers and rooms for optimal usage of time, where provider availability is matched with customized variables. The customized variables may include one or more of visit complexity, average visit length, number of exam rooms, provider preference, non-physician resources, and/or other information. One or more newly defined optimized scheduling templates may be uploaded via an outbound connection back to the scheduling system.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
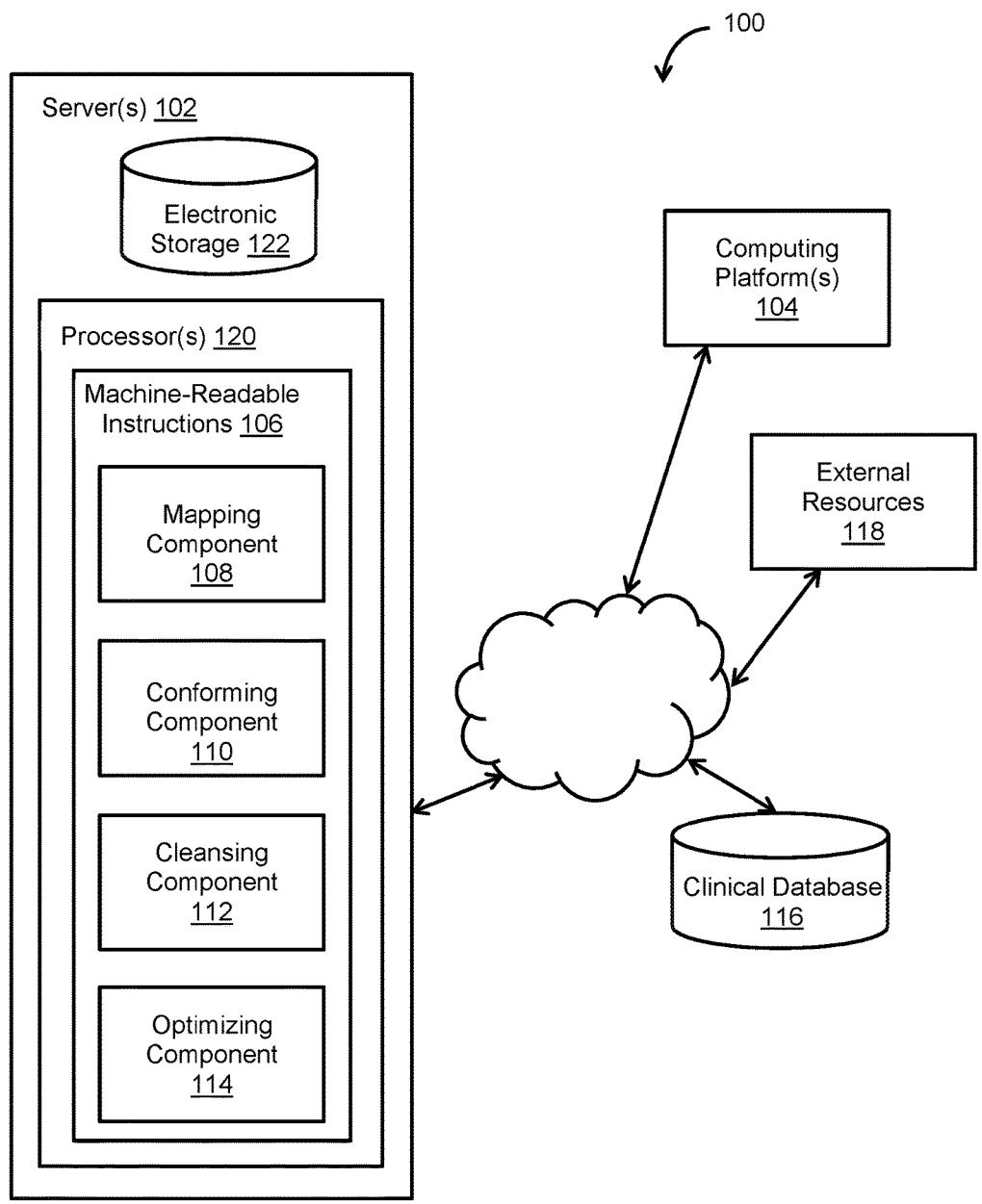
FIG. 1 illustrates a system for data cleansing to optimize clinical scheduling, in accordance with one or more implementations.

FIG. 1 illustrates a scheduling system 100 configured for data cleansing to optimize clinical scheduling system, in accordance with one or more implementations. In some implementations, scheduling system 100 may include one or more servers 102. The server(s) 102 may be configured to communicate with one or more computing platforms 104 according to client/server architecture, a peer-to-peer architecture, and/or other architectures. The users may access system 100 via computing platform(s) 104. A platform is an underlying computer system on which application programs can run.

The server(s) 102 may be configured to execute machine-readable instructions 106. The machine-readable instructions 106 may include one or more of a mapping component 106, a conforming component 110, a cleansing component 112, an optimizing component 114, and/or other machine-readable instruction components.

The machine-readable instructions 106 may be executable to provide a subject scheduling optimization suite that improves schedule utilization and subject flow. Exemplary implementations of the present technology may provide an intelligent scheduling platform that is effective in a variety of subject clinic settings. Exemplary implementations of the present technology include one or more of an inbound connection to any scheduling database, a standardized format of universal data elements from scheduling data, cleansing component 112 that purges data, such as for example historical data including data errors, optimization component 114 that leverages legacy data to be analyzed with configurable logic and provide optimized scheduling templates, an outbound connection back to the scheduling system to upload newly defined scheduling templates, and/or other components.

As mentioned herein, exemplary implementations of the present technology may include cleansing component 112. As opposed to other scheduling products that rely on custom interface and API work for each electronic medical record, exemplary implementations of the present technology may include a platform configured to force data from other systems to be conformed to its own standardized scheduling elements. This allows exemplary implementations of the present technology to be compatible with any electronic medical record with significantly less work.

Exemplary implementations of the present technology may provide a platform built on, for example, a star schema extensible framework. The star schema extensible framework may include one or more fact tables referencing any number of dimension tables. The fact tables may include one or more of numerical values or information regarding where descriptive information is kept, and/or other information. The dimension tables may include one or more of records with attributes to describe the fact data, and/or other information. A central, or primary, fact table may include standardized scheduling elements including one or more of appointment information, subject and provider keys, scheduling start and end times, and/or other information. According to some implementations, there is only one primary fact table in system 100. The primary fact table may sit at the center of the scheduling star schema of scheduling system 100. The primary fact table contains the relevant primary scheduling data for system 100. Within this primary fact table are keys that join to other tables that provide dimensional information.

In some exemplary implementations, the primary fact table may contain the fact that subject Joe Smith had an appointment on Wednesday, Mar. 23, 2016 at 2:00 p.m. Relevant information related to Joe Smith's demographic information is not typically stored in this primary fact table; however, in some implementations it may be. Typically, the relevant information would instead be stored in a separate table and keyed to the primary fact table by a primary field such as a patient ID (or subject ID). Thus, Joe Smith's scheduling information is keyed and joined to his demographic information within the scheduling model.

In some implementations according to the present technology, a standardized central fact table may be created that has conformed dimensions. This standardized central fact table may be assigned a logical name, such as, for example, F_Schedule_Retro. The name F_Schedule_Retro refers to the fact legacy retrospective table of schedule data. Standardized dimensional tables may be built with detail information such as appointment outcome information including one or more of appointment statuses, actual start times, actual end times, and/or other information. Subject and provider dimensional tables may be included with details that may include one or more of subject demographics, provider specialty information, and/or other information.

Figure 2:
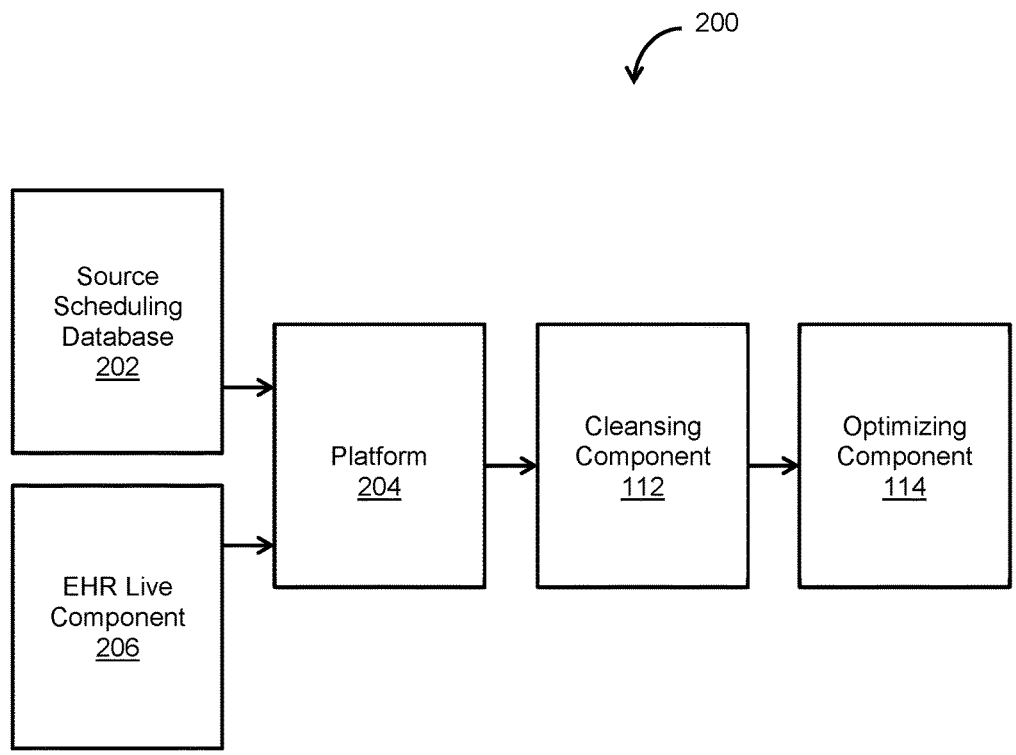
FIG. 2 illustrates a data cleansing structure, in accordance with one or more implementations.

FIG. 2 illustrates a data cleansing structure 200, in accordance with one or more implementations. Arrows in FIG. 2 show an exemplary flow of data through data cleansing structure 200. Clinical record data may be received from a source scheduling database 202, such as clinical database 116 of FIG. 1. The clinical record data may be extracted via one or more of an object linking and embedding database (OLEDB), an open database connectivity (ODBC) system, an API, and/or other techniques. OLEDB and ODBC connectors are standard database connectors commonly used to access data from Microsoft structured query language (SQL) or Oracle databases. These are the most common databases used for legacy scheduling data. However, it is contemplated that other types of databases may be used in various implementations according to the present technology. For non-standard databases, APIs or other connectors may be used to extract data and conformed to the products standard.

Once this data is in the desired format, a cleansing component 112 may perform user configurable cleansing actions. Examples of these actions may include the cleansing of data errors including rows of data missing documentation, to data artifacts in the form of data for a clinic that no longer exists. Business logic like ignoring all data from Thursdays, for example, may be performed at this stage in cleansing component 112.

Source scheduling database 202 may be communicatively coupled with platform 204 of the present disclosure. EHR live component 206 may also be communicatively coupled with platform 204. Platform 202 may be communicatively coupled with cleansing component 112, or may include cleansing component 112. Thus, source scheduling database 202 and EHR live component 206 may be communicatively coupled with cleansing component 112. In some implementations, components such as EHR live component 206 may be directly connected to cleansing component 112. Ergo, the present technology may advantageously allow for being able to directly pull data (e.g., clinical record data) from a live system (EHR live component 206). This technique allows for taking care of real-time or near real-time scheduling needs. One or more of platform 204, cleansing component 112, and/or other components may be communicatively coupled with optimizing component 114.

Clinical record data that is excluded from optimization component 114 may be stored for analytics and reporting, allowing insight into the types and amounts of data that are being excluded from analysis (metadata). Data that is cleansed may be fed to optimization component 114 for further analysis (machine learning).

In some implementations, platform 204 may be extensible so that inclusion of new data elements may be accomplished quickly with little added overhead. Newly requested elements may be created and then mapped from source data, via mapping component 108, and be run through optimizing component 114, leveraging configurable cleansing logic.

In some implementations, platform 204 may require data to be in the format shown in Table 1, in accordance with one or more implementations. Note that instances of the term "patient" in the tables (e.g., PatientKey in Table 1) could be generally though of as "subject" (e.g., SubjectKey). Table 1 is the central fact table, and resides at the center of the model for the process in some implementations.

There are several problems inherent to computer systems that are addressed by the present technology. Once within platform 204, cleansing component 112 may begin its work. Cleansing component 112 may provide standard cleansing functions to, for example, ignore data that is incomplete. In some implementations, source scheduling database 202 may be a legacy system. A legacy system includes one or more of an old method, technology, outdated computer system, application program, and/or other system. Referencing a system as "legacy" often implies that the system is out of date or in need of replacement. It is common to refer to a system that has been turned off already, but for which the data is still being used for analytics, as a legacy system.

Advantageously, implementations according to the present technology work with any source scheduling database 202, including legacy systems, without the need for various APIs or the like. Advantageously, since scheduling system 100 works with any existing electronic medical record, this enables clinics or other entities to maximize subject flow with existing staff and facilities. A further advantage provided is the synchronization of data from legacy systems, which is something that typically is not done currently. This

TABLE 1

(25) (Desired Format)

| PatientKey | ProviderKey | ClinicKey | ScheduleStart | ScheduleEnd | ActualStart | ActualEnd |
|---|---|---|---|---|---|---|

A prospective organization may have data from their electronic record in the format shown in one or both of Table 2, Table 3, or another format, in accordance with one or more implementations.

TABLE 2

(27) (Appointment Scheduled Table)

| APPT_KEY | PAT_ID | APPT_PROV_ID | DEPT_ID | APPT_SCHED_S | APPT_SCHED_E |
|---|---|---|---|---|---|

TABLE 3

(28) (Appointment Actual Table)

| APPT_KEY | APPT_START | APPT_END |
|---|---|---|

The prospective organization's data may be extracted and mapped to the desired format, as shown in Table 4, in accordance with one or more implementations.

paradigm provides a holistic picture of legacy scheduling data instead of a piecemeal picture based on an origin of a system. Clinics have several challenges when faced with limited personnel and resources that continue to diminish in the increasingly difficult healthcare environment. Many providers struggle to find the balance between operational efficiency that requires possible double-booking (or triple-booking etc.) of subjects to accommodate potential no-shows and subject satisfaction that might suffer from resulting longer wait-times or decreased schedule availability. Without the proper clinical intelligence, both subjects and operations suffer. Implementations according to the present technology solve these technical problems. A data-driven

TABLE 4

(30)

| PAT_ID | APPT_PROV_ID | DEPT_ID | APPT_SCHED_S | APPT_SCHED_E | APPT_START | APPT_END |
|---|---|---|---|---|---|---|

The data map may appear as shown in Table 5, in accordance with one or more implementations.

approach is provided to optimize clinic scheduling. Provider satisfaction is improved by normalizing subject flow and

TABLE 5

(32)

| PAT_ID | APPT_PROV_ID | DEPT_ID | APPT_SCHED_S | APPT_SCHED_E | APPT_START | APPT_END |
|---|---|---|---|---|---|---|
| PatientKey | ProviderKey | ClinicKey | ScheduleStart | ScheduleEnd | ActualStart | ActualEnd | aligning clinic operations. Subject satisfaction is improved by reducing wait times and enhancing appointment availability. Efficiency is improved by generating clinic performance metrics and increasing productivity and asset utilization. Staff may be happier due to more efficient and accurate scheduling. Subjects may be happier due to decreased wait times and optimized staff availability. Better operational effectiveness may translate to improved revenue and resource forecasting.

Appointment information such as, for example, legacy appointment information (from a legacy system) that is missing actual start or end times may be ignored so as not to impact analysis and generation of scheduling templates downstream. Some implementations may be configured to allow custom configuration to cleanse data from inclusion into optimization component 114 for other reasons.

In some exemplary implementations, a prospective organization may desire to ignore all appointments completed by "Dr. Smith" who retired earlier in the summer. Dr. Smith's Provider Key may be 1131, for example.

A portion of the prospective organization's data may be extracted and conformed to look as shown in Table 6.

TABLE 6

(38)

| PatientKey | ProviderKey | ClinicKey | ScheduleStart | ScheduleEnd | ActualStart | ActualEnd |
|---|---|---|---|---|---|---|
| 100125 | 1131 | 101 | 6/8/15 8:00 | 6/8/15 8:30 | 6/8/15 8:09 | 6/8/15 8:34 |
| 100159 | 1125 | 101 | 6/8/15 8:30 | 6/8/15 9:30 | | 6/8/15 9:50 |
| 101123 | 1189 | 101 | 6/8/15 9:00 | 6/8/15 9:30 | 6/8/15 9:03 | 6/8/15 9:37 |
| 111346 | 1167 | 101 | 6/8/15 9:00 | 6/8/15 9:30 | 6/8/15 9:00 | 6/8/15 9:32 |
| 100583 | 1192 | 101 | 6/8/15 8:00 | 6/8/15 9:00 | 6/8/15 8:01 | 6/8/15 9:20 |
| 107888 | 1158 | 101 | 6/8/15 11:00 | 6/8/15 11:30 | 6/8/15 11:13 | 6/8/15 11:50 |
| 113689 | 1136 | 101 | 6/8/15 10:00 | 6/8/15 11:00 | 6/8/15 10:07 | 6/8/15 10:44 |
| 123482 | 1131 | 101 | 6/8/15 9:00 | 6/8/15 9:30 | 6/8/15 8:55 | 6/8/15 9:15 |
| 186321 | 1258 | 101 | 6/8/15 8:00 | 6/8/15 8:30 | 6/8/15 8:22 | 6/8/15 8:48 |
| 100931 | 1479 | 101 | 6/8/15 9:00 | 6/8/15 10:00 | 6/8/15 9:13 | 6/8/15 10:01 |
| 103546 | 1189 | 101 | 6/8/15 8:00 | 6/8/15 8:30 | 6/8/15 8:01 | |
| 161001 | 1158 | 101 | 6/8/15 9:00 | 6/8/15 9:30 | 6/8/15 9:00 | 6/8/15 9:30 |

In some implementations, cleansing component 112 may address common data errors such as, for example, data with missing information (see Table 7).

TABLE 7

(40)

| PatientKey | ProviderKey | ClinicKey | ScheduleStart | ScheduleEnd | ActualStart | ActualEnd |
|---|---|---|---|---|---|---|
| 100125 | 1131 | 101 | 6/8/15 8:00 | 6/8/15 8:30 | 6/8/15 8:09 | 6/8/15 8:34 |
| 100159 | 1125 | 101 | 6/8/15 8:30 | 6/8/15 9:30 | | 6/8/15 9:50 |
| 101123 | 1189 | 101 | 6/8/15 9:00 | 6/8/15 9:30 | 6/8/15 9:03 | 6/8/15 9:37 |
| 111346 | 1167 | 101 | 6/8/15 9:00 | 6/8/15 9:30 | 6/8/15 9:00 | 6/8/15 9:32 |
| 100583 | 1192 | 101 | 6/8/15 8:00 | 6/8/15 9:00 | 6/8/15 8:01 | 6/8/15 9:20 |
| 107888 | 1158 | 101 | 6/8/15 11:00 | 6/8/15 11:30 | 6/8/15 11:13 | 6/8/15 11:50 |
| 113689 | 1136 | 101 | 6/8/15 10:00 | 6/8/15 11:00 | 6/8/15 10:07 | 6/8/15 10:44 |
| 123482 | 1131 | 101 | 6/8/15 9:00 | 6/8/15 9:30 | 6/8/15 8:55 | 6/8/15 9:15 |
| 186321 | 1258 | 101 | 6/8/15 8:00 | 6/8/15 8:30 | 6/8/15 8:22 | 6/8/15 8:48 |
| 100931 | 1479 | 101 | 6/8/15 9:00 | 6/8/15 10:00 | 6/8/15 9:13 | 6/8/15 10:01 |
| 103546 | 1189 | 101 | 6/8/15 8:00 | 6/8/15 8:30 | 6/8/15 8:01 | |
| 161001 | 1158 | 101 | 6/8/15 9:00 | 6/8/15 9:30 | 6/8/15 9:00 | 6/8/15 9:30 |

The appointments highlighted in bold/italics may be removed from data that will be passed on to optimization component 114. The prospective organization may request that Dr. Smith (having provider key 1131) be removed from inclusion in analysis.

These lines may be cleansed from inclusion in optimization component 114 (see Table 8).

TABLE 8

(43)

| PatientKey | ProviderKey | ClinicKey | ScheduleStart | ScheduleEnd | ActualStart | ActualEnd |
|---|---|---|---|---|---|---|
| 100125 | 1131 | 101 | 6/8/15 8:00 | 6/8/15 8:30 | 6/8/15 8:09 | 6/8/15 8:34 |
| 100159 | 1125 | 101 | 6/8/15 8:30 | 6/8/15 9:30 | | 6/8/15 9:50 |
| 101123 | 1189 | 101 | 6/8/15 9:00 | 6/8/15 9:30 | 6/8/15 9:03 | 6/8/15 9:37 |
| 111346 | 1167 | 101 | 6/8/15 9:00 | 6/8/15 9:30 | 6/8/15 9:00 | 6/8/15 9:32 |
| 100583 | 1192 | 101 | 6/8/15 8:00 | 6/8/15 9:00 | 6/8/15 8:01 | 6/8/15 9:20 |
| 107888 | 1158 | 101 | 6/8/15 11:00 | 6/8/15 11:30 | 6/8/15 11:13 | 6/8/15 11:50 |

TABLE 8-continued (43)

| PatientKey | ProviderKey | ClinicKey | ScheduleStart | ScheduleEnd | ActualStart | ActualEnd |
|---|---|---|---|---|---|---|
| 113689 | 1136 | 101 | 6/8/15 10:00 | 6/8/15 11:00 | 6/8/15 10:07 | 6/8/15 10:44 |
| 123482 | 1131 | 101 | 6/8/15 9:00 | 6/8/15 9:30 | 6/8/15 8:55 | 6/8/15 9:15 |
| 186321 | 1258 | 101 | 6/8/15 8:00 | 6/8/15 8:30 | 6/8/15 8:22 | 6/8/15 8:48 |
| 100931 | 1479 | 101 | 6/8/15 9:00 | 6/8/15 10:00 | 6/8/15 9:13 | 6/8/15 10:01 |
| 103546 | 1189 | 101 | 6/8/15 8:00 | 6/8/15 8:30 | 6/8/15 8:01 | |
| 161001 | 1158 | 101 | 6/8/15 9:00 | 6/8/15 9:30 | 6/8/15 9:00 | 6/8/15 9:30 |

The result is shown in Table 9, in accordance with one or more implementations.

TABLE 9

(45)

| PatientKey | ProviderKey | ClinicKey | ScheduleStart | ScheduleEnd | ActualStart | ActualEnd |
|---|---|---|---|---|---|---|
| 101123 | 1189 | 101 | 6/8/15 9:00 | 6/8/15 9:30 | 6/8/15 9:03 | 6/8/15 9:37 |
| 111346 | 1167 | 101 | 6/8/15 9:00 | 6/8/15 9:30 | 6/8/15 9:00 | 6/8/15 9:32 |
| 100583 | 1192 | 101 | 6/8/15 8:00 | 6/8/15 9:00 | 6/8/15 8:01 | 6/8/15 9:20 |
| 107888 | 1158 | 101 | 6/8/15 11:00 | 6/8/15 11:30 | 6/8/15 11:13 | 6/8/15 11:50 |
| 113689 | 1136 | 101 | 6/8/15 10:00 | 6/8/15 11:00 | 6/8/15 10:07 | 6/8/15 10:44 |
| 186321 | 1258 | 101 | 6/8/15 8:00 | 6/8/15 8:30 | 6/8/15 8:22 | 6/8/15 8:48 |
| 100931 | 1479 | 101 | 6/8/15 9:00 | 6/8/15 10:00 | 6/8/15 9:13 | 6/8/15 10:01 |
| 161001 | 1158 | 101 | 6/8/15 9:00 | 6/8/15 9:30 | 6/8/15 9:00 | 6/8/15 9:30 |

It is envisioned that periodic (e.g., weekly etc.) dashboard report customized templates may be provided.

Returning to FIG. 1, in some implementations, server(s) 102, computing platform(s) 104, and/or external resources 118 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, computing platform(s) 104, and/or external resources 118 may be operatively linked via some other communication media.

A given computing platform 104 may include one or more processors configured to execute machine-readable instructions. The machine-readable instructions may be configured to enable an expert or user associated with the given computing platform 104 to interface with system 100 and/or external resources 130, and/or provide other functionality attributed herein to computing platform(s) 104. By way of non-limiting example, the given computing platform 104 may include one or more of a desktop computer, a laptop computer, a handheld computer, a tablet computing platform, a NetBook, a Smartphone, a gaming console, and/or other computing platforms.

External resources 118 may include sources of information, hosts and/or providers of block chain environments outside of system 100, external entities participating with system 100, and/or other resources. In some implementations, some or all of the functionality attributed herein to external resources 118 may be provided by resources included in system 100.

Server(s) 102 may include electronic storage 122, one or more processors 120, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 122 may comprise non-transitory storage media that electronically stores information. The electronic storage media of electronic storage 122 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 120, information received from server(s) 102, information received from computing platform(s) 104, and/or other information that enables server(s) 102 to function as described herein.

Processor(s) 120 may be configured to provide information processing capabilities in server(s) 102. As such, processor(s) 120 may include one or more of a digital processor, an analog processor, a digital circuit designed to process information, an analog circuit designed to process information, a state machine, and/or other mechanisms for electronically processing information. Although processor(s) 120 is shown in FIG. 1 as a single entity, this is for illustrative purposes only. In some implementations, processor(s) 120 may include a plurality of processing units. These processing units may be physically located within the same device, or processor(s) 120 may represent processing functionality of a plurality of devices operating in coordination. The processor(s) 134 may be configured to execute machine-readable instruction components 108, 110, 112, 114, and/or other machine-readable instruction components. Processor(s) 120 may be configured to execute machine-readable instruction components 108, 110, 112, 114, and/or other machine-readable instruction components by software; hardware; firmware; some combination of software, hardware, and/or firmware; and/or other mechanisms for configuring processing capabilities on processor(s) 120. As used herein, the term "machine-readable instruction component" may refer to any component or set of components that perform the functionality attributed to the machine-readable instruction component. This may include one or more physical processors during execution of processor readable instructions, the processor readable instructions, circuitry, hardware, storage media, or any other components.

It should be appreciated that although machine-readable instruction components 108, 110, 112, 114 are illustrated in FIG. 1 as being implemented within a single processing unit, in implementations in which processor(s) 120 includes multiple processing units, one or more of machine-readable instruction components 108, 110, 112, and/or 114 may be implemented remotely from the other machine-readable instruction components. The description of the functionality provided by the different machine-readable instruction components 108, 110, 112, and/or 114 described herein is for illustrative purposes, and is not intended to be limiting, as any of machine-readable instruction components 108, 110, 112, and/or 114 may provide more or less functionality than is described. For example, one or more of machine-readable instruction components 108, 110, 112, and/or 114 may be eliminated, and some or all of its functionality may be provided by other ones of machine-readable instruction components 108, 110, 112, and/or 114. As another example, processor(s) 120 may be configured to execute one or more additional machine-readable instruction components that may perform some or all of the functionality attributed below to one of machine-readable instruction components 108, 110, 112, and/or 114.

Figure 3:
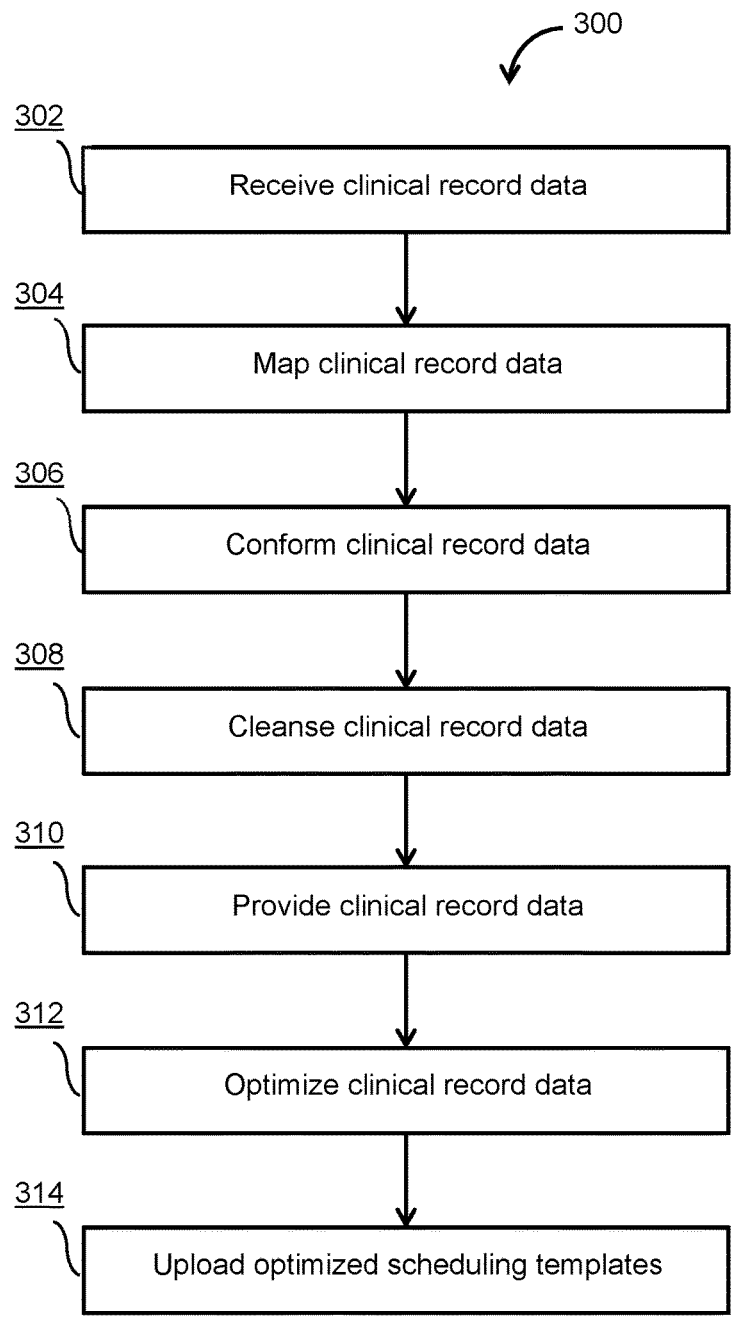
FIG. 3 illustrates a method for data cleansing to optimize clinical scheduling, in accordance with one or more implementations.

FIG. 3 illustrates a method 300 for data cleansing to optimize clinical scheduling, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, one or more operations of method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, the clinical record data may be received, in an agnostic manner, at platform 204 from a system including a source scheduling database 202 containing clinical record data. In this context, agnostic may refer to something that is generalized so that it is interoperable among various systems. Source scheduling database 202 may be any database, and thus the clinical record data may be received in an agnostic manner.

At an operation 304, clinical record data is mapped to a desired format. The desired format may a plurality of fields.

At an operation 306, the clinical record data is conformed to standardized scheduling elements of the scheduling system by parsing the clinical record data. The parsing may include reformatting the clinical record data by assigning portions of the data to appropriate fields.

At an operation 308, the clinical record data is cleansed, in a manner configurable by a user, to purge portions of the clinical record data related to one or more of data errors, data artifacts, or business logic. By design, platform 204 may allow a rules engine (or rules component) to be used by an end-user to effectively filter out erroneous data. The logic may be designed to exclude data based on user-configured selections depending on the fact table's dimensions.

For example, "weekday" may be a resultant dimension in the scheduling fact data. A user may want to ignore any instances where Dr. Smith had appointments on Wednesdays since he usually does not work on Wednesdays. In this case, the user may be able to create a rule that says ignore data where Dr. Smith is a provider and the appointment weekday is a Wednesday.

Additionally, for clinics that allow walk-ins for urgent care, unscheduled add-on appointments could muddy data that is based on scheduled appointments being completed. In this case, an end-user would be able to create and apply a rule that states, ignore all data that coincides with appointments that are of type "add-on" or "urgent care."

At an operation 310, clinical record data is provided to optimizing component 114 for optimization of the clinical record data.

At an operation 312, the clinical record data is optimized by applying configurable logic to the clinical record data in order to provide one or more newly defined optimized scheduling templates that configure one or both of providers and/or rooms for optimal usage of time. Provider availability is matched with customized variables. The customized variables include one or more of visit complexity, average visit length, number of exam rooms, provider preference, non-physician resources, and/or other variables and/or information. Optimization component 114 may also include the ability for system- and user-defined rules to optimize schedules by resource (not just by provider).

In some implementations, the order of priority of rules may be modified in optimization component 114. Thus, if there is ever a conflict in the rules then a rule that is listed first may take precedence.

In one exemplary implementation, data has been cleansed and Dr. Williams desired an optimized schedule. He does not work Wednesday afternoons and he would prefer to take longer appointments Wednesday mornings when he does work. Historical data may show that Dr. Williams averages seven 45-minute appointments per week and three 60-minute appointments per week. The schedule may be blocked off such that Dr. Williams is slated to work from 8:00 a.m. until 12:00 p.m. The ordering of the appointments thus may include assigning the three 60-minute appointments (scheduling his time until 11:00 a.m.), and then attempting to fit in two 45-minute appointments. However, do so would overbook the schedule to 12:30 p.m. instead of the desired time of 12:00 p.m. Instead, system 100 recognizes the hard stop at 12:00 p.m. and inserts three 20-minute appointment blocks.

At an operation 314, one or more newly defined optimized scheduling templates are uploaded via an outbound connection back to scheduling system 100.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A scheduling system configured for data cleansing to optimize clinical scheduling, the system comprising:
one or more hardware processors of a clinical scheduling system configured by machine-readable instructions to:
receive clinical record data, in an agnostic manner, from a system including a source scheduling database containing the clinical record data, wherein:
received clinical record data is received in one of a plurality of different formats the clinical scheduling system is configured to operatively accept for purposes of optimizing scheduling templates,
received clinical record data is received from at least two tables in the source scheduling database,
received clinical record data includes a plurality of appointment records corresponding to historical clinical appointments,
at least some of the appointment records include data from each of the at least two tables in the source scheduling database, and
at least some of the appointment records including a plurality of appointment-record fields, the appointment-record fields for each of the at least some appointment records comprising a respective patient identifier, a respective provider identifier, a respective scheduled appointment start time, a respective actual appointment start time, a respective scheduled appointment end time, and a respective actual appointment end time;
map the clinical record data to a desired format, the desired format including a plurality of fields of standardized scheduling elements of the clinical scheduling system, wherein mapping comprises mapping respective appointment-record fields to corresponding fields of the standardized scheduling elements;
based on the mapping, conform the clinical record data to standardized scheduling elements of the scheduling system by parsing the clinical record data and reformatting the clinical record data by assigning portions of the data to appropriate fields to form the standardized scheduling elements from the appointment records, wherein a given standardized scheduling element has fields stored in a single table of the clinical scheduling system from each of at least two tables in the source scheduling database;
cleanse, in a manner configurable by a user, the clinical record data to filter out portions of the clinical record data, wherein cleansing comprises:
determining whether to exclude data of at least some appointment records based on whether the respective appointment records omit a given field;
determining whether to exclude data of at least some appointment records based on whether the respective appointment records include a given provider identifier; and
determining whether to exclude data of at least some appointment records based on whether the respective appointment records correspond to one or more durations of time;
provide the standardized scheduling elements to an optimization engine for optimization of provider and facility scheduling templates based on the clinical record data;
optimize, with the optimization engine, the provider and facility scheduling templates by applying configurable logic to the standardized scheduling elements in order to provide one or more at least partially newly defined optimized scheduling templates that configure both of providers and rooms for improved usage of time relative to un-optimized scheduling templates, wherein optimizing comprises:
matching provider availability with customized variables, the customized variables based on visit complexity, visit length, number of exam rooms, provider preference, and non-physician resources;
optimizing at least some of the scheduling templates for providers matched with the customized variables based on user-defined rules to optimize schedules; and
detecting and resolving a conflict in the user-defined rules to optimize schedules; and
generate one or more communications configured to upload one or more at least partially newly defined optimized scheduling templates via an outbound connection back to the scheduling system, wherein:
the scheduling system includes subject and provider dimensional tables with details that include one or both of subject demographics or provider specialty information;
the one or more hardware processors are further configured by machine-readable instructions to extract data from the source scheduling database or other source scheduling databases via an OLEDB connection, an ODBC connection, and another application program interface (API); and
the one or more hardware processors are further configured by machine-readable instructions to cleanse data errors including rows of data missing information, wherein:
the one or more hardware processors are further configured by machine-readable instructions to populate a primary fact table of data of the clinical scheduling system surrounded by dimensional tables of the clinical scheduling system, the primary fact table of data including appointment information, subject and provider keys, appointment scheduling start times, and appointment scheduling end times, the dimensional tables including subject dimensional tables and provider dimensional tables, and
the dimensional tables include standardized dimensional tables that comprise detail information that includes appointment outcome information having appointment statuses, actual appointment start times, and actual appointment end times, and wherein subject and provider dimensional tables include detail information that includes both of subject demographics and provider specialty information.

2. The system of claim 1, wherein conforming the clinical record data allows the scheduling system to work with any electronic medical record.

3. The system of claim 1, wherein the one or more hardware processors are further configured by machine-readable instructions to utilize a star schema extensible framework, the star schema extensible framework including one or more fact tables referencing a plurality of dimension tables, the fact tables including one or both of numerical values or information regarding where descriptive information is kept, or the dimension tables including records with attributes to describe the fact data.

4. The system of claim 1, wherein the one or more hardware processors are further configured by machine-readable instructions to run one or more cleansing functions to ignore data that is incomplete, appointment information that is missing a start time, and appointment information that is missing an end time.

5. The system of claim 1, wherein data that is excluded from the optimization engine is stored for analytics and reporting, and wherein the clinical scheduling system is configured to generate one or more reports on types and amounts of data that are being excluded from analysis, the types and amounts of data that are being excluded from analysis including one or more of data with missing information, data that is not relevant, data that is incomplete, or data that is erroneous.

6. A scheduling method configured for data cleansing to optimize clinical scheduling, the method being performed by one or more hardware processors configured by machine-readable instructions, the method comprising:

receiving clinical record data, with one or more processors of a clinical scheduling system, in an agnostic manner, from a system including a source scheduling database containing the clinical record data, wherein:
  received clinical record data is received in one of a plurality of different formats the clinical scheduling system is configured to operatively accept for purposes of optimizing scheduling templates,
  received clinical record data is received from at least two tables in the source scheduling database,
  received clinical record data includes a plurality of appointment records corresponding to historical clinical appointments,
  at least some of the appointment records include data from each of the at least two tables in the source scheduling database, and
  at least some of the appointment records including a plurality of appointment-record fields, the appointment-record fields for each of the at least some appointment records comprising a respective patient identifier, a respective provider identifier, a respective scheduled appointment start time, a respective actual appointment start time, a respective scheduled appointment end time, and a respective actual appointment end time;

mapping, with one or more processors of the clinical scheduling system, the clinical record data to a desired format, the desired format including a plurality of fields of standardized scheduling elements of the clinical scheduling system, wherein mapping comprises mapping respective appointment-record fields to corresponding fields of the standardized scheduling elements;

based on the mapping, conforming, with one or more processors of the clinical scheduling system, the clinical record data to standardized scheduling elements of the scheduling system by parsing the clinical record data and reformatting the clinical record data by assigning portions of the data to appropriate fields to form the standardized scheduling elements from the appointment records, wherein a given standardized scheduling element has fields stored in a single table of the clinical scheduling system from each of at least two tables in the source scheduling database;

cleansing, with one or more processors of the clinical scheduling system, in a manner configurable by a user, the clinical record data to filter out portions of the clinical record data, wherein cleansing comprises:
  determining whether to exclude data of at least some appointment records based on whether the respective appointment records omit a given field;
  determining whether to exclude data of at least some appointment records based on whether the respective appointment records include a given provider identifier; and
  determining whether to exclude data of at least some appointment records based on whether the respective appointment records correspond to one or more durations of time;

providing, with one or more processors of the clinical scheduling system, the standardized scheduling elements to an optimization engine for optimization of provider and facility scheduling templates based on the clinical record data;

optimizing, with one or more processors of the clinical scheduling system, the provider and facility scheduling templates by applying configurable logic to the standardized scheduling elements in order to provide one or more at least partially newly defined optimized scheduling templates that configure one or both of providers and rooms for improved usage of time relative to un-optimized scheduling templates, wherein optimizing comprises:
  matching provider availability with customized variables, the customized variables based on visit complexity, visit length, number of exam rooms, provider preference, and non-physician resources;
  optimizing at least some of the scheduling templates for providers matched with the customized variables based on user-defined rules to optimize schedules; and
  detecting and resolving a conflict in the user-defined rules to optimize schedules; and generating, with one or more processors of the clinical scheduling system, one or more communications configured to upload one or more newly defined optimized scheduling templates via an outbound connection back to the scheduling system, wherein:

the scheduling system includes subject and provider dimensional tables with details that include one or both of subject demographics or provider specialty information;

the one or more hardware processors are further configured by machine-readable instructions to extract data from the source scheduling database or other source scheduling databases via an OLEDB connection, an ODBC connection, and another application program interface (API); and the one or more hardware processors are further configured by machine-readable instructions to cleanse data errors including rows of data missing information, wherein:

the one or more hardware processors are further configured by machine-readable instructions to populate a primary fact table of data of the clinical scheduling system surrounded by dimensional tables of the clinical scheduling system, the primary fact table of data including appointment information, subject and provider keys, appointment scheduling start times, and appointment scheduling end times, the dimensional tables including subject dimensional tables and provider dimensional tables, and the dimensional tables include standardized dimensional tables that comprise detail information that includes appointment outcome information having appointment statuses, actual appointment start times, and actual appointment end times, and wherein subject and provider dimensional tables include detail information that includes both of subject demographics and provider specialty information.

7. The method of claim 6, wherein conforming the clinical record data allows the scheduling system to work with any electronic medical record.

8. The method of claim 6, wherein the one or more hardware processors are further configured by machine-readable instructions to utilize a star schema extensible framework, the star schema extensible framework including one or more fact tables referencing a plurality of dimension tables, the fact tables including one or both of numerical values or information regarding where descriptive information is kept, or the dimension tables including records with attributes to describe the fact data.

9. The method of claim 6, wherein the one or more hardware processors are further configured by machine-readable instructions to run one or more cleansing functions to ignore data that is incomplete, appointment information that is missing a start time, and appointment information that is missing an end time.

10. The method of claim 6, wherein data that is excluded from the optimization engine is stored for analytics and reporting, and wherein the clinical scheduling system is configured to generate one or more reports on types and amounts of data that are being excluded from analysis, the types and amounts of data that are being excluded from analysis including one or more of data with missing information, data that is not relevant, data that is incomplete, or data that is erroneous.

11. A scheduling system configured for data cleansing to optimize clinical scheduling, the system comprising:
one or more hardware processors of a clinical scheduling system configured by machine-readable instructions to:
receive clinical record data, in an agnostic manner, from a system including a source scheduling database containing the clinical record data, wherein:
received clinical record data is received in one of a plurality of different formats the clinical scheduling system is configured to operatively accept for purposes of optimizing scheduling templates,
received clinical record data is received from at least two tables in the source scheduling database,
received clinical record data includes a plurality of appointment records corresponding to historical clinical appointments,
at least some of the appointment records include data from each of the at least two tables in the source scheduling database, and
at least some of the appointment records including a plurality of appointment-record fields, the appointment-record fields for each of the at least some appointment records comprising a respective patient identifier, a respective provider identifier, a respective scheduled appointment start time, a respective actual appointment start time, a respective scheduled appointment end time, and a respective actual appointment end time;
map the clinical record data to a desired format, the desired format including a plurality of fields of standardized scheduling elements of the clinical scheduling system, wherein mapping comprises mapping respective appointment-record fields to corresponding fields of the standardized scheduling elements;
based on the mapping, conform the clinical record data to standardized scheduling elements of the scheduling system by parsing the clinical record data and reformatting the clinical record data by assigning portions of the data to appropriate fields to form the standardized scheduling elements from the appointment records, wherein a given standardized scheduling element has fields stored in a single table of the clinical scheduling system from each of at least two tables in the source scheduling database;
cleanse, in a manner configurable by a user, the clinical record data to filter out portions of the clinical record data, wherein cleansing comprises:
determining whether to exclude data of at least some appointment records based on whether the respective appointment records omit a given field;
determining whether to exclude data of at least some appointment records based on whether the respective appointment records include a given provider identifier; and
determining whether to exclude data of at least some appointment records based on whether the respective appointment records correspond to one or more durations of time;
provide the standardized scheduling elements to an optimization engine for optimization of provider and facility scheduling templates based on the clinical record data;
optimize, with the optimization engine, the provider and facility scheduling templates by applying configurable logic to the standardized scheduling elements in order to provide one or more at least partially newly defined optimized scheduling templates that configure both of providers and rooms for improved usage of time relative to un-optimized scheduling templates, wherein optimizing comprises:
matching provider availability with customized variables, the customized variables based on visit complexity, visit length, number of exam rooms, provider preference, and non-physician resources;
optimizing at least some of the scheduling templates for providers matched with the customized variables based on user-defined rules to optimize schedules; and
detecting and resolving a conflict in the user-defined rules to optimize schedules; and
generate one or more communications configured to upload one or more at least partially newly defined optimized scheduling templates via an outbound connection back to the scheduling system, wherein:

the scheduling system includes subject and provider dimensional tables with details that include one or both of subject demographics or provider specialty information;

the one or more hardware processors are further configured by machine-readable instructions to extract data from the source scheduling database or other source scheduling databases via an OLEDB connection, an ODBC connection, and another application program interface (API); and the one or more hardware processors are further configured by machine-readable instructions to cleanse data errors including rows of data missing information, wherein:

data that is excluded from the optimization engine is stored for analytics and reporting, and wherein the clinical scheduling system is configured to generate one or more reports on types and amounts of data that are being excluded from analysis, the types and amounts of data that are being excluded from analysis including one or more of data with missing information, data that is not relevant, data that is incomplete, or data that is erroneous.

12. A scheduling method configured for data cleansing to optimize clinical scheduling, the method being performed by one or more hardware processors configured by machine-readable instructions, the method comprising:

receiving clinical record data, with one or more processors of a clinical scheduling system, in an agnostic manner, from a system including a source scheduling database containing the clinical record data, wherein:

received clinical record data is received in one of a plurality of different formats the clinical scheduling system is configured to operatively accept for purposes of optimizing scheduling templates, received clinical record data is received from at least two tables in the source scheduling database, received clinical record data includes a plurality of appointment records corresponding to historical clinical appointments, at least some of the appointment records include data from each of the at least two tables in the source scheduling database, and at least some of the appointment records including a plurality of appointment-record fields, the appointment-record fields for each of the at least some appointment records comprising a respective patient identifier, a respective provider identifier, a respective scheduled appointment start time, a respective actual appointment start time, a respective scheduled appointment end time, and a respective actual appointment end time;

mapping, with one or more processors of the clinical scheduling system, the clinical record data to a desired format, the desired format including a plurality of fields of standardized scheduling elements of the clinical scheduling system, wherein mapping comprises mapping respective appointment-record fields to corresponding fields of the standardized scheduling elements;

based on the mapping, conforming, with one or more processors of the clinical scheduling system, the clinical record data to standardized scheduling elements of the scheduling system by parsing the clinical record data and reformatting the clinical record data by assigning portions of the data to appropriate fields to form the standardized scheduling elements from the appointment records, wherein a given standardized scheduling element has fields stored in a single table of the clinical scheduling system from each of at least two tables in the source scheduling database;

cleansing, with one or more processors of the clinical scheduling system, in a manner configurable by a user, the clinical record data to filter out portions of the clinical record data, wherein cleansing comprises:

determining whether to exclude data of at least some appointment records based on whether the respective appointment records omit a given field;

determining whether to exclude data of at least some appointment records based on whether the respective appointment records include a given provider identifier; and determining whether to exclude data of at least some appointment records based on whether the respective appointment records correspond to one or more durations of time;

providing, with one or more processors of the clinical scheduling system, the standardized scheduling elements to an optimization engine for optimization of provider and facility scheduling templates based on the clinical record data;

optimizing, with one or more processors of the clinical scheduling system, the provider and facility scheduling templates by applying configurable logic to the standardized scheduling elements in order to provide one or more at least partially newly defined optimized scheduling templates that configure one or both of providers and rooms for improved usage of time relative to un-optimized scheduling templates, wherein optimizing comprises:

matching provider availability with customized variables, the customized variables based on visit complexity, visit length, number of exam rooms, provider preference, and non-physician resources;

optimizing at least some of the scheduling templates for providers matched with the customized variables based on user-defined rules to optimize schedules; and detecting and resolving a conflict in the user-defined rules to optimize schedules; and generating, with one or more processors of the clinical scheduling system, one or more communications configured to upload one or more newly defined optimized scheduling templates via an outbound connection back to the scheduling system, wherein:

the scheduling system includes subject and provider dimensional tables with details that include one or both of subject demographics or provider specialty information;

the one or more hardware processors are further configured by machine-readable instructions to extract data from the source scheduling database or other source scheduling databases via an OLEDB connection, an ODBC connection, and another application program interface (API); and the one or more hardware processors are further configured by machine-readable instructions to cleanse data errors including rows of data missing information, wherein:

data that is excluded from the optimization engine is stored for analytics and reporting, and wherein the clinical scheduling system is configured to generate one or more reports on types and amounts of data that are being excluded from analysis, the types and amounts of data that are being excluded from analysis including one or more of data with missing information, data that is not relevant, data that is incomplete, or data that is erroneous.

* * * * *